(12) United States Patent
Kobayashi et al.

(10) Patent No.: US 11,116,955 B2
(45) Date of Patent: Sep. 14, 2021

(54) METHOD FOR PRODUCING MICRONEEDLE DEVICE

(71) Applicant: HISAMITSU PHARMACEUTICAL CO., INC., Tosu (JP)

(72) Inventors: Toru Kobayashi, Tosu (JP); Toshiyuki Matsudo, Tsukuba (JP); Shinpei Nishimura, Tsukuba (JP); Seiji Tokumoto, Tsukuba (JP); Tetsuji Kuwahara, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/488,450

(22) PCT Filed: Feb. 20, 2018

(86) PCT No.: PCT/JP2018/005985
§ 371 (c)(1),
(2) Date: Aug. 23, 2019

(87) PCT Pub. No.: WO2018/155433
PCT Pub. Date: Aug. 30, 2018

(65) Prior Publication Data
US 2019/0381300 A1   Dec. 19, 2019

(30) Foreign Application Priority Data

Feb. 24, 2017 (JP) .............................. JP2017-033782

(51) Int. Cl.
*A61M 37/00*     (2006.01)

(52) U.S. Cl.
CPC . *A61M 37/0015* (2013.01); *A61M 2037/0053* (2013.01); *A61M 2205/0238* (2013.01)

(58) Field of Classification Search
None
See application file for complete search history.

(56) References Cited

U.S. PATENT DOCUMENTS 6,656,147 B1 * 12/2003 Gertsek ............ A61M 5/14248
604/185
8,632,801 B2 * 1/2014 Ameri .................... B65B 55/00
424/449

(Continued)

FOREIGN PATENT DOCUMENTS

CN    1562402 A     1/2005
CN   101076409 A   11/2007

(Continued)

OTHER PUBLICATIONS

International Search Report dated Mar. 20, 2018 corresponding to application No. PCT/JP2018/005985.

(Continued)

*Primary Examiner* — Cachet I Proctor
(74) *Attorney, Agent, or Firm* — Nath, Goldberg & Meyer; Joshua B. Goldberg

(57) ABSTRACT

A method for producing a microneedle device having a coating on the microneedles comprises a step A of drying a precursor composition containing a biologically active substance and a first solvent to obtain -a freeze-dried composition, a step B of mixing the freeze-dried composition with a second solvent to obtain a coating composition, and a step C of applying the coating composition to the microneedles and drying the same, wherein the precursor composition further contains a thickener, or a thickener is added when the freeze-dried composition and the second solvent are mixed.

16 Claims, 2 Drawing Sheets

(56) References Cited

U.S. PATENT DOCUMENTS

| | | | | |
|---|---|---|---|---|
| 2008/0213461 A1* | 9/2008 | Gill | ................... | A61K 9/0021 427/2.3 |
| 2014/0276474 A1* | 9/2014 | Ding | ................... | A61P 29/00 604/289 |

FOREIGN PATENT DOCUMENTS

| | | | | | |
|---|---|---|---|---|---|
| CN | 101102809 | A | | 1/2008 | |
| CN | 104080441 | A | | 10/2014 | |
| CN | 104800191 | A | * | 7/2015 | |
| CN | 105498082 | A | | 4/2016 | |
| EP | 2822540 | | | 1/2015 | |
| EP | 3195859 | A1 | | 7/2017 | |
| JP | 2013-177376 | A | | 9/2013 | |
| JP | 2013177376 | A | * | 9/2013 | ........ A61M 37/0015 |
| JP | 2015-509529 | A | | 3/2015 | |
| KR | 20150119204 | A | | 10/2015 | |
| WO | 2012115207 | A1 | | 8/2012 | |
| WO | 2013133702 | A1 | | 9/2013 | |
| WO | 2016043323 | A1 | | 3/2016 | |

OTHER PUBLICATIONS

Chen, Jianmin, et al. "Controllable Coating of Microneedles for Transdermal Drug Delivery"; Drug Development and Industrial Pharmacy; 2015; 41(3), 2015, p. 415-p. 422.

Nireesha GR, et al., "Lyophilization/Freeze Drying—An Review", International Journal of Novel Trends in Pharmaceutical Sciences 2013; 3(4), 2013, p. 87-p. 98.

Office Action dated Dec. 13, 2019 corresponding to Taiwanese application No. 107106079.

European Search Report dated Nov. 10, 2020 corresponding to Patent Application No. 18756585.8.

Korean Office Action dated Jan. 26, 2021 corresponding to Patent Application No. 10-2019-7023578.

Chinese Office Action dated Jan. 28, 2021 corresponding to Patent Application No. 201880013269.X.

Chinese Office Action dated Jul. 12, 2021 corresponding to application No. 201880013269.X.

* cited by examiner

METHOD FOR PRODUCING MICRONEEDLE DEVICE

This is a National Phase Application filed under 35 U.S.C. 371 as a national stage of PCT/JP2018/005985, filed Feb. 20, 2018, an application claiming the benefit of Japanese Application No. 2017-033782, filed Feb. 24, 2017, the content of each of which is hereby incorporated by reference in its entirety.

TECHNICAL FIELD

The present invention relates to method for producing a microneedle device.

BACKGROUND ART

A microneedle device is a substrate equipped with a plurality of microneedles, the microneedles having a coating layer containing a. biologically active substance in the vicinity of the tip. A microneedle device is an external preparation to be applied such that the microneedles are brought into contact with the skin of a user. After application, the biologically active substance contained in the coating layer spreads into the subcutanedus tissue, so that the pharmacological effect of the biologically active substance is exhibited.

A microneedle device is typically produced by providing a substrate equipped with microneedles and applying a coating composition containing a biologically active substance in the vicinity of the tip of the microneedles (for example, Patent Literature 1).

Incidentally, the amount of the coating composition applied to one microneedle device is very small. An increase in the amount of a solvent in the coating composition, however, may result in the case where a sufficient viscosity for the coating layer to be retained in the vicinity of the tip cannot be secured during formation of the layer. Under the circumstances, conventional methods for producing a microneedle device employ a method in which an amount more than the required amount of the coating composition is prepared and the redundant coating composition is dumped.

CITATION LIST

Patent Literature

Patent Literature 1: JP 2013-177376 A

SUMMARY OF INVENTION

Technical Problem

The coating layer is administered into the living body of a user, and the coating composition needs to be subjected to sterilization treatment in the same manner as with injections for sanitary reasons. In conventional methods for producing a microneedle device, the redundant coating composition is, therefore, required to be subjected to sterilization treatment, resulting in economic burden.

On the other hand, it is required for a biologically active substance to be efficiently dissolved in a smaller amount of solvent in order to reduce the amount of the coating composition to be prepared to a desired level. Uniform mixing of a small amount of highly viscous coating composition is, however, extremely difficult.

An object of the present invention is, therefore, to provide an efficient method for producing a microneedle device.

Solution to Problem

Through extensive investigation, the present inventors have found that a required amount of a coating composition can be efficiently prepared by drying a composition containing a biologically active substance to prepare a freeze-dried composition, and mixing the resulting freeze-dried composition with a solvent.

In other words, the present invention relates to a method for producing a microneedle device having a coating layer on microneedles, comprising a step A of drying a precursor composition containing a biologically active substance and a first solvent to obtain a freeze-dried composition, a step B of mixing the freeze-dried composition with a second solvent to obtain a coating composition, and a step C of applying the coating composition to the microneedles and consequently drying the same, wherein the precursor composition further contains a thickener, or a thickener is added when the freeze-dried composition and the second solvent are mixed.

With use of a freeze-dried composition obtained by drying the precursor composition containing a biologically active substance and a first solvent, the amount of a second solvent for use in preparation of a coating composition can be reduced.

It is preferable that the bulk volume of the freeze-dried composition be 3 to 110 times the volume of the second solvent. With a volume ratio in the range, a highly viscous coating composition can be obtained, allowing the thickness to be controlled to a desired level when the microneedles are coated with the composition.

It is preferable that the viscosity of the coating composition be 1000 to 25000 cps. With a viscosity in the range, dripping can be minimized when the microneedles are coated with the composition.

It is preferable that the density of the freeze-dried composition be 6 to 140 mg/L. With a density of the freeze-dried composition in the range, the biologically active substance is easily dissolved when mixed with a second solvent, so that a more uniform coating composition can be obtained.

It is preferable that in the step B, the freeze-dried composition and the second solvent be mixed using a planetary centrifugal mixer. With use of a planetary centrifugal mixer, mixing can be more efficiently achieved and the resulting coating composition hardly adheres to the wall surface of a container.

It is preferable that the step C be dip coating.

Advantageous Effects of Invention

According to the present invention, a microneedle device can be efficiently prepared. Specifically, the present invention allows not only a biologically active substance to be efficiently dissolved even in a small amount of solvent, but also a highly viscous coating composition to be prepared corresponding to a desired amount, so that dumping of a redundant coating composition is not required.

DESCRIPTION OF EMBODIMENTS

Figure 1:
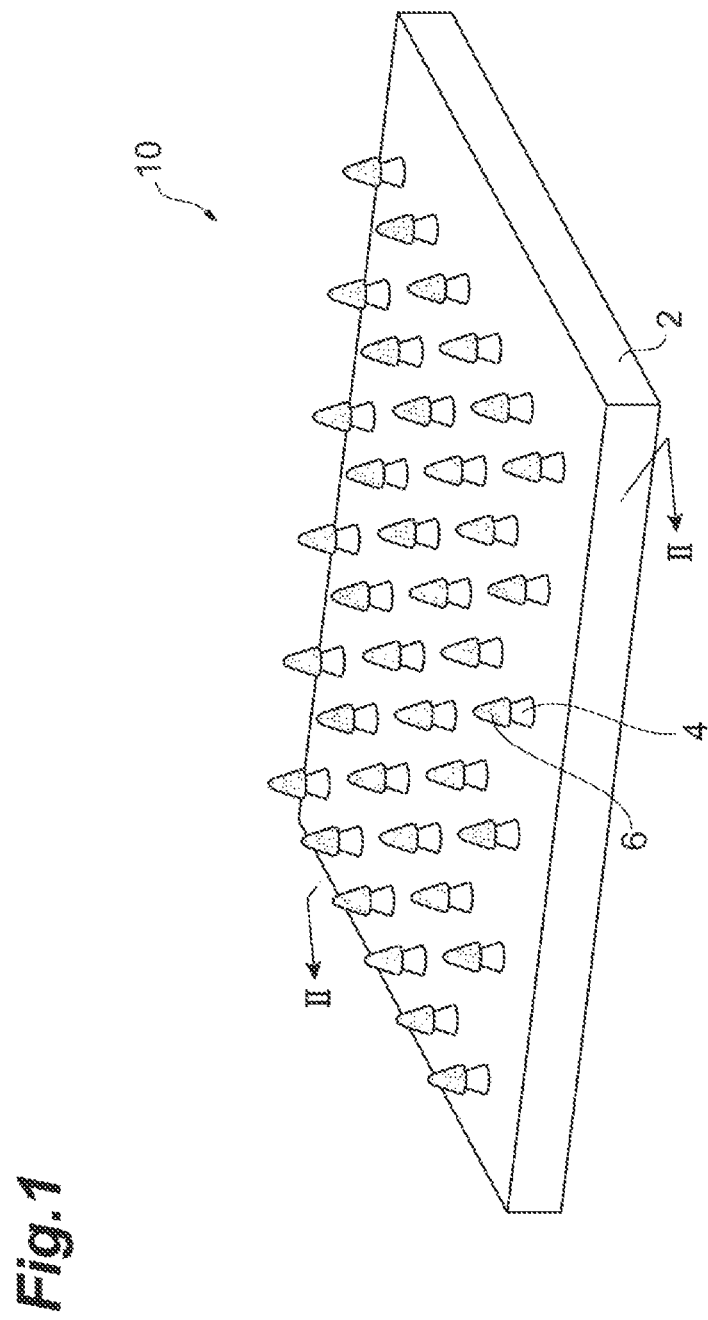
FIG. 1 is a perspective view showing a microneedle device in an embodiment.

With reference to drawings, preferred embodiments are described as follows. Incidentally, in the description of drawings, the same symbols are used for the same elements, and redundant descriptions are omitted. Further, the drawing is partially exaggerated for easy understanding, so that the dimension ratios do not necessarily correspond to the description.

The microneedle device is described as follows.

FIG. 1 is a perspective view showing the microneedle device as an example. A microneedle device 10 shown in FIG. 1 comprises a substrate 2, a plurality of microneedles 4 disposed on the main surface of the substrate 2, and a coating layer 6 formed on the microneedles 4. The coating layer 6 contains a biologically active substance and a thickener. In the present specification, a structure having a plurality of microneedles 4 formed on the substrate 2 is referred to as a microneedle array. As the microneedle array, a conventionally known microneedle array can be used. The detail of the microneedle array is described below as an example.

The substrate 2 is a foundation for supporting the microneedles 4. The shape of the substrate 2 is not particularly limited, and, for example, in a rectangular shape or a circular shape and in a flat form or a curved form. The area of the substrate 2 is preferably 0.5 to 10 cm², more preferably 1 to 5 cm², still more preferably 1 to 3 cm². A plurality of the substrates 2 may be connected to constitute a substrate having a desired size.

The microneedle 4 denotes a convex structure, more specifically, a needle shape in the broad meaning or a structure including a needle shape. The microneedle 4 is not limited to a structure having a needle shape with a pointed end, and may be in a shape with a rounded end. The shape of the microneedle 4 is, for example, a polygonal pyramid shape such as a quadrangular pyramid shape or a conical shape. In the case where the microneedle 4 is in a conical structure, it is preferable that the diameter at the base be about 50 to 200 μm. The microneedle 4 is a microstructure having a length (height) $H_M$ of preferably 50 to 600 μm. With a length $H_M$ of the microneedle 4 of 50 μm or more, administration of a biologically active substance contained in the coating layer can be more reliable. Also, with a length $H_M$ of the microneedle 4 of 600 μm or less, contact of the microneedle 4 with a nerve is avoided, so that the possibility of occurrence of pain can be reduced and the possibility of bleeding can be avoided. Further, with a length of the microneedle 4 of 500 μm or less, the amount of a biologically active substance can be efficiently administered into intradermal sites, and can also be administered without perforation of the basement membrane. It is particularly preferable that the length $H_M$ of the microneedle 4 be 300 to 500 μm.

The microneedles 4 are arranged, for example, in a square lattice form, a rectangular lattice form, an orthorhombic lattice form, a 45-degree staggered form, or a 60-degree staggered form. From the perspective of efficient introduction of a biologically active substance in the coating layer 6 into the skin, the number of the microneedles 4 per 1 cm² of a substrate may be 10 to 10000, and the number is preferably 20 to 5000, more preferably 50 to 500.

Examples of the material of the substrate 2 or the microneedle 4 include silicon, silicon dioxide, ceramics, metals, polysaccharides, and synthesized or natural resin materials. Examples of the metals include stainless steel, titanium, nickel, molybdenum, chromium and cobalt. As the resin materials, a biodegradable polymer such as a polylactic acid, a polyglycolide, a polylactic acid-co-polyglycolide, caprolactone, a polyurethane and a polyanhydride, and a non-degradable polymer such as a polycarbonate, a polymethacrylate, ethylene vinyl acetate, a polytetralkoroethylene and a polyoxymethylene are suitable. Further, polysaccharides such as hyaluronic acid, sodium hyaluronate, dextran, dextrin and chondroitin sulfate are also suitable.

The coating layer 6 may be formed on all of the plurality of microneedles 4 that exist, or may be formed on a part of the microneedles 4. The coating layer 6 may be formed on a tip part only of the microneedle 4, or may be formed to cover the whole of the microneedle 4. The average thickness of the coating layer 6 may be less than 50 μm, or may be μm to 30 μm.

Examples of the method for producing a substrate 2 or microneedles 4 include wet etching or dry etching of a silicon substrate, and precision machining of metal or resin (e.g., electrical discharge machining, laser processing, dicing, hot embossing and injection molding) and cutting. Through the processing method, the substrate 2 and the microneedles 4 are integrally formed. Examples of the method for making the microneedles 4 hollow include a secondary processing by laser or the like after production of the microneedles 4.

Figure 2:
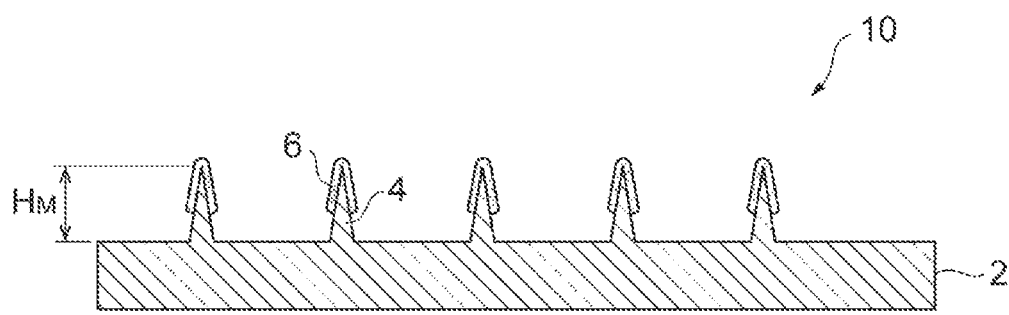
FIG. 2 is a cross-sectional view taken from line II-II of FIG. 1.

FIG. 2 is a side cross-sectional view taken from line II-II of FIG. 1. As shown in FIG. 2, a microneedle device 1 comprises a substrate 2, microneedles 4 disposed on the main surface of the substrate 2, and a coating layer 6 formed on the microneedles 4. The coating layer 6 formed on the microneedles contains a biologically active substance and a thickener.

A method for producing a microneedle device having a coating layer on microneedles in an embodiment of the present invention comprises a step A of drying a precursor composition containing a biologically active substance and a first solvent to obtain a freeze-dried composition, a step B of mixing the freeze-dried composition with a second solvent to obtain a coating composition, and a step C of applying the coating composition to the microneedles and drying the same, wherein the precursor composition further contains a thickener, or a thickener is added when the freeze-dried composition and the second solvent are mixed.

The step A in the present embodiment is a step of drying a precursor composition containing a biologically active substance and a first solvent to obtain a freeze-dried composition.

The biologically active substance in the present specification is a substance exhibiting therapeutic or preventive effect for a subject to whom the substance is administered. Examples of the biologically active substance include peptides, proteins, DNAs, RNAs, sugars, nucleic acids and glycoproteins. In particular, in the case where the biologically active substance is made of glycoprotein, the coating layer can be more efficiently formed.

Specific examples of the biologically active substance include interferon α, interferon β for multiple sclerosis, erythropoietin, follitropin β, follitropin α, G-CSF, GM-CSF, human chorionic hormone, leutinizing hormone, follicle-stimulating hormone (FSH), calcitonin salmon, glucagon, GNRH antagonist, insulin, LHRH (luteinizing hormone releasing hormone), human growth hormone, parathyroid hormone (PTH), filgrastim, heparin, low-molecular weight heparin, somatropin, incretin, GLP-1 analogues e.g., exenatide, liraglutide, lixisenatide, albiglutide and taspoglutide), snake venom peptide analogue, γ globulin, Japanese encephalitis vaccine, rotavirus vaccine, Alzheimer's disease vaccine, arteriosclerosis vaccine, cancer vaccine, nicotine vaccine, diphtheria vaccine, tetanus vaccine, pertussis vaccine, Lyme disease vaccine, rabies vaccine, pneumococcus vaccine, yellow fever vaccine, cholera vaccine, vaccinia vaccine, tuberculosis vaccine, rubella vaccine, measles vaccine, influenza vaccine, mumps vaccine, botulinum vaccine, herpes virus vaccine, other DNA vaccines, hepatitis B vaccine, and Japanese encephalitis vaccine.

The first solvent is not particularly limited, so long as the solvent can dissolve the biochemical active substance without causing a chemical reaction with the biochemical active substance. In order to dry the first solvent during preparation of the freeze-dried composition from a precursor composition, the boiling point of the solvent is preferably 150° C. or less, more preferably 80 to 120° C. With a boiling point of 120° C. or less, the dry solvent is easily removed, so that the preparation of the freeze-dried composition is more easily made. In particular, in the case where the biologically active substance is made of protein or nucleic acid, the biologically active substance may cause thermal decomposition. With a boiling point of the first solvent of 150° C. or less, a high temperature or a high degree of vacuum is not required during drying, so that the decomposition of the biologically active substance is easily suppressed.

Examples of the first solvent include water, cyclohexane and acetic acid.

The amount of the biologically active substance contained in the precursor composition relative to 100 parts of the precursor composition may be, for example, 0.1 to 30 parts by mass, and is preferably 0.2 to 15 parts by mass. Also, the amount of the first solvent contained in the precursor composition relative to 100 parts by mass of the precursor composition may be 70 to 99.9 parts by mass, and is preferably 80 to 99.9 parts by mass, more preferably 90 to 99.9 parts by mass.

The precursor composition may comprise a biologically active substance and a first solvent only, or may further contain a thickener or other biologically inactive components.

In the case where the precursor composition contains a thickener, the amount of the thickener which may be contained in the precursor composition relative to 100 parts by mass of the precursor composition may by 0.1 to 15 parts by mass, and is preferably 0.2 to 10 parts by mass, more preferably 0.3 to 5 parts by mass.

In the case where the thickener is a compound in a solid form at ordinary temperature, it is preferable that the thickener be added to the precursor composition. Through addition of the thickener to the precursor composition, the freeze-dried composition contains the thickener, so that the thickener is easily dissolved in the second solvent in the step B. Further, since the thickener is dispersed into the whole freeze-dried composition, the viscosity of the coating composition tends to be uniform. In the case where the precursor composition contains a solid thickener, it is preferable that the first solvent can dissolve the thickener. Examples of such a first solvent include water, cyclohexane and acetic acid.

Ordinary temperature in the present specification is the same as that defined in the present industrial field, which is usually 15° C. to 25° C.

Examples of the solid thickener include basic amino acids and water-soluble polymers. Examples of the preferred basic amino acid include arginine, histidine and lysine. Examples of the preferred polymer include chondroitin sulfate, pullulan, polyvinyl alcohol, dextran and polyvinylpyrrolidone.

In the case where the thickener is a compound in a liquid form at ordinary temperature, it is preferable that the amount of the thickener is controlled to 0.3 to 2 parts by mass relative to 100 parts by mass of the precursor composition. With an amount of the thickener in the range, the freeze-dried composition has good formability. In the ease where the precursor composition contains a liquid thickener, it is preferable that the first solvent be excellent in compatibility with the thickener.

Examples of the liquid thickener include glycerin, propylene glycol, lactic acid, benzyl alcohol and butylene glycol.

The amount of the biologically inactive components contained in the precursor composition is, for example, 0.01 to 5 parts by mass relative to 100 parts by mass of the precursor composition. Examples of the biologically inactive components include a base material, a stabilizer, a pH adjuster, and other components (e.g., components for accelerating migration of drugs into blood, a surfactant, oils and fats, and inorganic substances).

The base material performs function of retaining the coating composition to the microneedles, being effective for easily applying the composition to the microneedles. Examples of the base material include water-soluble polymers such as polysaccharides, cellulose derivatives, biodegradable polyesters, biodegradable polyamino acids, polyethylene oxide, polyvinyl alcohol, and polyvinylpyrrolidone, or sugars and sugar alcohols. These base materials may be used alone, or may be used in a combination of two or more thereof.

The stabilizer performs function of preventing each component to be oxidized by oxygen or photo-oxidized, so that the biologically active substance is stabilized. Examples of the stabilizer include L-cysteine, sodium pyrosulfite, sodium hydrogen sulfite, ascorbic acid, ethylenediamine tetraacetic acid (EDTA) or salts thereof, and dibutylhydroxytoluene (BHT) These stabilizers may be used alone or may be used in a combination of two or more thereof As the pH adjuster, ones typically usable in the present industrial field can be used. Examples of the pH adjuster include an inorganic acid or an organic acid, an alkali, a salt, an amino acid or a combination thereof. Specific examples of the pH adjuster include an organic acid such as tartaric acid, fumaric acid, citric acid and benzoic acid; an inorganic acid such as hydrochloric acid, phosphoric acid and sulfuric acid; an organic base such as trometamol, meglumine and ethanol amine; and an inorganic base such as sodium hydroxide, potassium hydroxide, magnesium hydroxide and calcium hydroxide. These pH adjusters may be used alone, or may be used in a combination of two or more thereof The freeze-dried composition may be produced by freeze-drying a precursor composition. Freeze-drying can not only avoid the precursor composition from exposure to a high temperature, but also enables a spongy freeze-dried composition having a larger surface area to he prepared because the first solvent is sublimed after the precursor composition is once frozen. With a larger surface area of the freeze-dried composition, the contact area with the second solvent increases in the step B, so that the solubility of the freeze-dried composition is further improved.

The freeze-dried composition in the present specification is not a simple lump solid composition in a dry state, but each of the components of the freeze-dried composition is not in a crystalline state (being in an amorphous state).

The amount of the biologically active substance contained in the freeze-dried composition relative to 100 parts by mass of the freeze-dried composition is preferably 1 to 100 parts by mass, more preferably 5 to 100 parts by mass. In the case where the freeze-dried composition contains a thickener, the amount of the thickener contained in the freeze-dried composition relative to 100 parts by mass of the freeze-dried composition is preferably 10 to 80 parts by mass, more preferably 20 to 70 parts by mass.

The density of the freeze-dried composition is preferably 6 to 140 mg/mL, more preferably 7 to 100 mg/mL, particularly preferably 8 to 70 mg/mL. With a density of the freeze-dried composition of less than 6 mg/mL, the strength of the freeze-dried composition decreases, so that handling of the composition tends to be difficult. With a density of the freeze-dried composition of more than 140 mg/mL, few voids are present in the freeze-dried composition, so that the solubility and the rate of dissolution in the second solvent may decrease in some cases.

The step B in the present embodiment is a step of mixing the freeze-dried composition with a second solvent to obtain a coating composition.

As the freeze-dried, composition, a composition obtained in the step A can be used. The freeze-dried composition may be pulverized to a desired size prior to the use in the step B.

The second solvent and the first solvent may be the same as each other, or may be different from each other. Examples of the second solvent include water, glycerin, propylene glycol, lactic acid, benzyl alcohol and butylene glycol.

In the step B, mixing is performed such that the bulk volume of the freeze-dried composition is preferably 3 to 110 times the volume of the second solvent, more preferably 5 to 100 times, particularly preferably 10 to 100 times. In the case where the bulk volume of the freeze-dried composition is less than 3 times the volume of the second solvent, the resulting coating composition has a reduced viscosity, easily causing dripping during application to the microneedles. Further, in formation of the coating layer on the microneedles, the amount of the coating composition tends to be redundant. On the other hand, in the case where the bulk volume of the freeze-dried composition is more than 110 times the volume of the second solvent, the biologically active substance is hardly dissolved.

When the freeze-dried composition and the second solvent are mixed, a thickener may be added. The thickener which can be added in the step B may be the same thickener defined in the step A. In the case Where the thickener is a compound in a liquid form at ordinary temperature, it is preferable that the thickener is added when the coating composition is prepared. With addition of the liquid thickener during preparation of the coating composition, the formability of the freeze-dried composition needs not be considered, and mixing with the second solvent can be easily achieved. In the case where the thickener is a liquid compound at ordinary temperature, it is preferable that the second solvent be excellent in compatibility with the thickener.

A thickener may be added when the precursor composition is prepared in the step A, when the coating composition is prepared in the step B, or at both times. For example, after preparation of the freeze-dried composition with addition of a solid thickener during preparation of the precursor composition, a liquid thickener may be added during preparation of the coating composition.

It is preferable that the mixture of the freeze-dried composition and the second solvent be sufficiently stirred with an agitator in the preparation of the coating composition. Examples of the agitator include a Vortex mixer, a centrifuge, a shaker, a dissolver with impeller blade, a three-axis planetary mixer, and a planetary centrifugal mixer. A preferred agitator is a three-axis planetary mixer or a planetary centrifugal mixer, and a more preferred agitator is a planetary centrifugal mixer. A planetary centrifugal mixer is a mixer which operates such that a container containing materials is revolved clockwise while the container is rotated anticlockwise at the same time. The stirring by a three-axis planetary mixer or a planetary centrifugal mixer allows the biologically active substance contained in the freeze-dried composition to be easily dissolved in the second solvent, so that a small amount of a highly viscous coating composition can be easily prepared.

When the coating composition is prepared, stirring under reduced pressure is preferred. Mixing of the coating composition under reduced pressure allows bubbles in, the coating composition to be removed, so that chips or voids hardly occur in the coating layer of a microneedle device. The presence of chips or voids in the coating layer may cause pain when a microneedle device is applied to the skin. In the case where the coating composition is stirred under reduced pressure, the pressure may be that less than one atmospheric pressure.

The viscosity of the coating composition can be adjusted by the mixing ratio between the freeze-dried composition and the second solvent, or the amount of a thickener. The viscosity of the coating composition is adjusted preferably to 1000 to 25000 cps, more preferably to 1500 to 15000 cps. With a viscosity of the coating composition of less than 1000 cps, dripping is easily caused during application to the microneedles. On the other hand, with a viscosity of the coating composition of more than 25000 cps, the biologically active substance in the coating composition is hardly uniformly dispersed.

The step C in the present embodiment is a step of applying the coating composition to the microneedles and drying the same.

In the step C, the coating composition may be applied to the microneedles one by one, or all the coating may be performed at once through dip-coating. In the case where dip-coating is performed, a plate with hollows arranged corresponding to the arrangement of the microneedles of a microneedle, array may be used. After filling the hollows arranged in the plate with the coating composition, the microneedle array and the plate are combined such that the microneedles fit in the hollows to perform coating. Through the dip-coating, the thickness of the coating layer on each of the microneedles tends to be uniform, so that the biologically active substance can be uniformly disposed over the entire microneedle device.

In the case of dip-coating, it is preferable that the rate of separating the microneedle array from the coating composition be controlled after dipping. The separating rate is preferably 0.1 to 200 mm/s, more preferably 0.5 to 100 mm/s, still more preferably 1 to 10 mm/s. With a separating rate of 0.1 to 200 mm/s, the thickness of the coating layer is more uniform, so that the amount of the coating composition applied to the microneedle array tends to be constant. Examples of the method for controlling the separating rate include a method for separating the microneedle array or a plate with the coating composition arranged thereon by using a motor-driven apparatus or a vacuum apparatus. In the case where separation is performed using a vacuum apparatus, the control can be made through appropriate change in the degree of vacuum and the distance between the microneedle array and the vacuum head.

After application of the coating composition to the microneedles, the second solvent is dried, so that the coating layer is formed on the microneedles. Drying may be performed under conditions enabling the second solvent to he removed. A preferred drying condition is air drying. Air drying allows the viscosity of the applied coating composition to decrease, so that the possibility of occurrence of dripping is further reduced.

EXAMPLES

Test Example 1

Solubility Test (1)

In Test Example 1, BSA (bovine serum albumin) was used as the biologically active substance, and pullulan was used as the thickener. In Preparation Examples 1 to 4, according to the description in Table 1, BSA, pullulan and water were mixed in a 2-mL centrifugal tube. In Preparation Examples 5 to 8, according to the description in Table 2, BSA and pullulan were dissolved in 1 mL of water in a 2-mL centrifugal tube, and the solution was then freeze-dried using a freeze-dryer to obtain a freeze-dried composition. Subsequently, the resulting freeze-dried composition was mixed with water. In Table 1 and Table 2, the numerical values denote mass (unit: mg) unless otherwise rioted, and the solid content concentration denotes the concentration (unit: %) of the solid content (BSA and pullulan) relative to the whole mixture.

TABLE 1

| | Biologically active substance BSA | Thickener Pullulan | Water | Solid content concentration (%) |
|---|---|---|---|---|
| Preparation Example 1 | 60 | 60 | 180 | 40 |
| Preparation Example 2 | 63 | 63 | 174 | 42 |
| Preparation Example 3 | 66 | 66 | 168 | 44 |
| Preparation Example 4 | 69 | 69 | 162 | 46 |

TABLE 2

| | Biologically active substance BSA | Thickener Pullulan | Water | Solid content concentration (%) |
|---|---|---|---|---|
| Preparation Example 5 | 60 | 60 | 180 | 40 |
| Preparation Example 6 | 63 | 63 | 174 | 42 |
| Preparation Example 7 | 66 | 66 | 168 | 44 |
| Preparation Example 8 | 69 | 69 | 162 | 46 |

The resulting mixture was stirred for 60 minutes with a planetary centrifugal mixer (brand name: AWATORINERI-TARO ARE500, manufactured by Thinky Corporation). As the stirring conditions, the revolution rate was set at 1500 rpm, and the rotation rate was set at 47 rpm. The presence or absence of insoluble matter in the mixture after stirring (coating composition) was visually observed.

In the mixtures in the Preparation Examples 1 to 4, insoluble matter was observed, while the mixtures in the Preparation Examples 5 to 8, no insoluble matter was observed. In other words, forming a freeze-dried composition and then dissolving the same in water improved the solubility of the biologically active substance and the thickener.

Test Example 2

Solubility Test (2)

In Test Example 2, BSA (bovine serum albumin) was used as the biologically active substance, and pullulan was used as the thickener. In Preparation Examples 9 to 14, according to the description in Table 3, BSA and pullulan were dissolved in 1 mL of water in a 2-mL centrifugal tube, and the solution was then freeze-dried using a freeze-dryer to obtain a freeze-dried composition. Subsequently, the resulting freeze-dried composition was mixed with water. The freeze-dried composition was prepared to have a bulk volume of 750 µL, regardless of the amounts of BSA and pullulan in Table 3, the numerical values denote mass (unit: mg) unless otherwise noted. The volume ratio is a value of the hulk volume of the freeze-dried composition (unit: divided by the volume of water (unit: µL).

TABLE 3

| | Biologically active substance BSA | Thickener Pullulan | Dried cake | | | Volume ratio |
|---|---|---|---|---|---|---|
| | | | Mass | Density [mg/mL] | Water | |
| Preparation Example 9 | 50 | 50 | 100 | 133.3 | 150.0 | 5.0 |
| Preparation Example 10 | 25 | 25 | 50 | 66.7 | 75.0 | 10.0 |
| Preparation Example 11 | 6.25 | 6.25 | 12.5 | 16.7 | 18.8 | 39.9 |
| Preparation Example 12 | 4.15 | 4.15 | 8.3 | 11.1 | 12.5 | 60.0 |
| Preparation Example 13 | 3.15 | 3.15 | 6.3 | 8.4 | 9.4 | 79.8 |
| Preparation Example 14 | 2.5 | 2.5 | 5 | 6.7 | 7.5 | 100.0 |

The resulting mixture was stirred for 60 minutes with a planetary centrifugal mixer (brand name: AWATORINERI-TARO ARE500, manufactured by Thinky Corporation). As the stirring conditions, the revolution rate was set at 1500 rpm, and the rotation rate was set at 47 rpm. The presence or absence of insoluble matter in the mixture after stirring (coating composition) was visually observed.

In any of the mixtures in the Preparation Examples 9 to 14, no insoluble matter was observed.

Test Example 3

Solubility Test (3)

In Preparation Examples 15 and 16, according to the description in Table 4, a biologically active substance was dissolved in 10 µL of water in a 2-mL centrifugal tube, and the solution was then freeze-dried using a freeze-dryer to obtain a freeze-dried composition. Subsequently, a thickener B and water were added to the resulting freeze-dried composition. In Preparation Examples 17 and 18, according to the description in Table 4, a biologically active substance and a thickener A were dissolved in 10 µL of water in a 2-mL centrifugal tube, and the solution was then freeze-dried using a freeze-dryer to obtain a freeze-dried composition. Subsequently, water was added to the resulting freeze-dried composition. In Table 4, the numerical values denote the content ratio (unit: mass %) of each component in the mixture after stirring (coating composition). The bulk volume of the freeze-dried composition was set at 800 µL.

TABLE 4

| | Dried cake | | | | | | |
|---|---|---|---|---|---|---|---|
| | Biologically active substance | | Thickener A | | Thickener B | | Water |
| | Component | Amount | Component | Amount | Component | Amount | Amount |
| Preparation Example 15 | Human serum albumin | 40 | — | — | Glycerin | 40 | 20 |
| Preparation Example 16 | PTH | 40 | — | — | Propylene glycol | 60 | 0 |
| Preparation Example 17 | Dexmedetomidine | 45 | Chondroitin sulfate | 20 | — | — | 35 |
| Preparation Example 18 | Risedronate | 35 | Arginine | 35 | — | — | 30 |

The resulting mixture was stirred for 60 minutes with a planetary centrifugal mixer (brand name: AWATORINERI-TARO ARE500, manufactured by Thinky Corporation). As the stirring conditions, the revolution rate was set at 1500 rpm, and the rotation rate was set at 47 rpm. The presence or absence of insoluble matter in the mixture after stirring (coating composition) was visually Observed.

In any of the mixtures in the Preparation Examples 15 to 18, no insoluble matter was observed.

Subsequently, the viscosity of each coating composition was measured using a small sample viscometer (brand name: Small Sample Viscometer VROC, manufactured by RheoSense, Inc.). The viscosities of the coating compositions obtained in the Preparation Examples 15 to 18 were 3476 cps, 23974 cps, 4997 cps and 1266 cps, respectively.

Test Example 4

Solubility Test (4)

In a Preparation Example 19, according to the description in. Table 5, 450 mg of a biologically active substance (human serum albumin) was dissolved in 90 mL of water in a 100-mL centrifugal tube, and the solution was then freeze-dried using a freeze-dryer to obtain a freeze-dried composition (density: 5 mg/mL). The bulk volume of the freeze-dried composition was set at 90 mL. To the resulting freeze-dried composition, a solution including 66 mg of arginine, 529 mg of glycerin and 13 mg of citric acid dissolved in 265 mg of water was added. In Table 5, the numerical values denote the content ratios (unit: mass %) of the respective components in the mixture after stirring (coating composition).

TABLE 5

| | Component | Content ratio |
|---|---|---|
| Dried cake | Human serum albumin | 34 |
| Thickener | Glycerin | 40 |
| Thickener | Arginine | 5 |
| pH adjuster | Citric acid | 1 |
| Solvent | Water | 20 |

The resulting mixture was stirred for 30 minutes with a planetary centrifugal mixer (brand name: AWATORINERI-TARO ARE500, manufactured by Thinky Corporation). As the stirring conditions, the revolution rate was set at 2000 rpm, and the rotation rate was set at 63 rpm. The presence or absence of insoluble matter in the mixture after stirring (coating composition) was visually observed.

In the mixture in the Preparation Example 19, no insoluble matter was observed.

REFERENCE SIGNS LIST

2: SUBSTRATE, 4: MICRONEEDLE, 6: COATING LAYER,
10: MICRONEEDLE DEVICE

The invention claimed is:

1. A method for producing a microneedle device having a coating on microneedles comprising:
   a step A of drying a precursor composition containing a biologically active substance and a first solvent to obtain a freeze-dried composition,
   a step B of mixing the freeze-dried composition with a second solvent to obtain a coating composition, and
   a step C of applying the coating composition to the microneedles and consequently drying, wherein
   the precursor composition further contains a thickener, or a thickener is added when the freeze-dried composition and the second solvent are mixed;
   wherein the second solvent is used in a reduced amount compared to if the freeze-dried composition was not required for preparation of the coating composition.

2. The method according to claim 1, wherein the step C is dip coating.

3. The method according to claim 1, wherein the freeze-dried composition has a bulk volume of 3 to 110 times the volume of the second solvent.

4. The method according to claim 3, wherein the coating composition has a viscosity of 1000 to 25000 cps.

5. The method according to claim 3, wherein the freeze-dried composition has a density of 6 to 140 mg/mL.

6. The method according to claim 3, wherein, in the step B, the freeze-dried composition and the second solvent are mixed using a planetary centrifugal mixer.

7. The method according to claim 3, wherein the step C is dip coating.

8. The method according to claim 1, wherein the coating composition has a viscosity of 1000 to 25000 cps.

9. The method according to claim 8, wherein the freeze-dried composition has a density of 6 to 140 mg/mL.

10. The method according to claim 8, wherein, in the step B, the freeze-dried composition and the second solvent are mixed using a planetary centrifugal mixer.

11. The method according to claim 8, wherein the step C is dip coating.

12. The method according to claim 1, wherein the freeze-dried composition has a density of 6 to 140 mg/mL.

13. The method according to claim 12, wherein, in the step B, the freeze-dried composition and the second solvent are mixed using a planetary centrifugal mixer.

14. The method according to claim 12, wherein the step C is dip coating.

15. The method according to claim 1, wherein, in the step B, the freeze-dried composition and the second solvent are mixed using a planetary centrifugal mixer.

16. The method according to claim 15, wherein the step C is dip coating.

\* \* \* \* \*